(12) United States Patent
Peticca et al.

(10) Patent No.: US 10,322,222 B2
(45) Date of Patent: Jun. 18, 2019

(54) INTEGRATED MEDICAL PUMP AND OXYGENATOR

(71) Applicant: Terumo Cardiovascular Systems Corporation, Ann Arbor, MI (US)

(72) Inventors: Louis F. Peticca, Elkton, MD (US); Christine T. Cordaro, Wilmington, DE (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 844 days.

(21) Appl. No.: 14/796,003

(22) Filed: Jul. 10, 2015

(65) Prior Publication Data

US 2017/0007755 A1    Jan. 12, 2017

(51) Int. Cl.
*A61M 1/00* (2006.01)
*A61M 1/16* (2006.01)
*A61M 1/10* (2006.01)

(52) U.S. Cl.
CPC ........ *A61M 1/1698* (2013.01); *A61M 1/1013* (2014.02); *A61M 2207/00* (2013.01)

(58) Field of Classification Search
CPC . A61M 1/1698; A61M 1/1013; A61M 1/1006
See application file for complete search history.

(56) References Cited

U.S. PATENT DOCUMENTS

| | | | |
|---|---|---|---|
| 5,040,944 A | 8/1991 | Cook | |
| 5,263,924 A | 11/1993 | Mathewson | |
| 5,266,256 A | 11/1993 | Jerman et al. | |
| 5,266,265 A * | 11/1993 | Raible | A61M 1/1698 210/321.6 |
| 5,270,005 A | 12/1993 | Raible | |
| 5,280,005 A | 1/1994 | Nakajima et al. | |
| 5,308,320 A * | 5/1994 | Safar | A61M 1/3621 604/113 |
| 5,411,706 A | 5/1995 | Hubbard et al. | |
| 5,578,267 A | 11/1996 | Cosentino et al. | |
| 5,591,404 A | 1/1997 | Mathewson | |
| 5,770,149 A | 6/1998 | Raible | |
| 5,830,370 A | 11/1998 | Maloney, Jr. et al. | |
| 6,379,618 B1 | 4/2002 | Piplani et al. | |
| 6,387,323 B1 | 5/2002 | Afzal et al. | |
| 6,428,747 B1 * | 8/2002 | Dueri | A61M 1/1698 422/46 |

(Continued)

FOREIGN PATENT DOCUMENTS

WO    2012/013925    2/2012

OTHER PUBLICATIONS

PCT International Search Report & Written Opinion dated Sep. 16, 2016 in corresponding International Application No. PCT/US16/41264, 7 pages.

(Continued)

*Primary Examiner* — Ariana Zimbouski
(74) *Attorney, Agent, or Firm* — Fish & Richardson P.C.

(57) ABSTRACT

Extracorporeal circuit devices that can be used for on-pump open-heart surgery to support surgical procedures such as coronary artery bypass grafting are described. In some embodiments, an oxygenator can include an integral pump. Such an integrated arrangement can advantageously provide an extracorporeal circuit with a lower overall volume than other conventional extracorporeal circuits.

10 Claims, 4 Drawing Sheets

(56) References Cited

U.S. PATENT DOCUMENTS

| | | |
|---|---|---|
| 8,622,950 B2 | 1/2014 | Lauber et al. |
| 8,795,591 B2 | 8/2014 | Roller et al. |
| 8,864,700 B2 | 10/2014 | Kawamura et al. |
| 2007/0249888 A1 | 10/2007 | Wu et al. |
| 2008/0234623 A1* | 9/2008 | Strauss ............... A61M 1/1698 604/6.11 |
| 2010/0272604 A1 | 10/2010 | Carpenter et al. |
| 2010/0272606 A1* | 10/2010 | Carpenter ........... A61M 1/1698 422/46 |
| 2010/0282604 A1 | 11/2010 | Inoue et al. |
| 2012/0193289 A1 | 8/2012 | Cloutier et al. |
| 2012/0308434 A1 | 12/2012 | Kawamura et al. |
| 2013/0094997 A1 | 4/2013 | Wang et al. |
| 2013/0343954 A1 | 12/2013 | Gartner et al. |

OTHER PUBLICATIONS

PCT International Preliminary Report on Patentability dated Jan. 16, 2018 in corresponding International Application No. PCT/US16/41264, 6 pages.

* cited by examiner

INTEGRATED MEDICAL PUMP AND OXYGENATOR

BACKGROUND

1. Technical Field

This document relates to devices used during surgical procedures for treatment of heart conditions. For example, this document relates to extracorporeal circuit devices that can be used for on-pump open-heart surgery to facilitate surgical procedures such as coronary artery bypass grafting.

2. Background Information

Hollow fiber oxygenators are utilized within the extracorporeal circuit to meet a patient's gas exchange needs during cardiopulmonary bypass surgery. Blood from the patient is either gravity drained, or VAVD (vacuum assisted venous drainage) is used to obtain the required amount of flow to maintain sufficient volume in a reservoir. A centrifugal pump coupled with a magnetic driver is sometimes used in the main line of the circuit in order to pump blood from the reservoir, through the oxygenator, and finally back to the patient.

Prior to the initiation of bypass, a crystalloid priming solution is pumped through the extracorporeal circuit to remove air. The crystalloid priming solution remains in the extracorporeal circuit prior to the patient's blood being introduced. Hemodilution occurs when the blood mixes with the priming solution, thereby reducing the concentration of red blood cells (i.e., the hematocrit or hemoglobin value). Extracorporeal circuit devices with low prime volumes are preferable as they reduce the overall hemodilution. Any reduction in prime volume within the extracorporeal circuit can have an impact on hemodilution. If excessive hemodilution occurs such that the patient's hematocrit drops below a critical value (as specified by the physician and/or institution), a red blood cell transfusion may be deemed necessary. Studies have indicated that both low hematocrit values (possibly caused by hemodilution) and red blood cell transfusions correlate to higher patient mortalities.

SUMMARY

This document provides devices used during surgical procedures for the treatment of heart conditions. For example, this document provides extracorporeal circuit devices that can be used for on-pump open-heart surgery to facilitate surgical procedures such as coronary artery bypass grafting. In some embodiments described herein, a blood oxygenator apparatus includes an integral pump. Such an integrated arrangement can advantageously provide an extracorporeal circuit with a lower overall volume than other conventional extracorporeal circuits. In some embodiments described herein, a blood oxygenator apparatus is selectively coupleable with an integral pump module or with another type of module.

In one implementation, a blood oxygenator apparatus includes an outer housing and a heat exchanger disposed within the outer housing. The heat exchanger defines an internal space. The blood oxygenator apparatus also includes an oxygenator disposed within the outer housing. The oxygenator is arranged concentrically around the heat exchanger. The blood oxygenator apparatus also includes a pump assembly disposed concentrically within the internal space. The pump assembly includes a rotary vane member that is rotatable in relation to the heat exchanger and the outer housing. The rotary vane member defines a maximum diameter and an axial length. In some embodiments, the axial length of the rotary vane member is greater than the maximum diameter of the rotary vane member.

Such a blood oxygenator apparatus may optionally include one or more of the following features. The pump assembly may be selectively coupleable with the outer housing. In some embodiments, a ratio of the axial length of the rotary vane member to the maximum diameter of the rotary vane member is greater than or equal to about 2:1.5. The blood oxygenator apparatus may also include a flow distribution element disposed within the internal space. In some embodiments, the flow distribution element is configured to facilitate a substantially uniform radial flow rate of blood entering the heat exchanger.

In another implementation, a blood oxygenator apparatus includes a heat exchanger defining an internal space, and an oxygenator arranged concentrically around the heat exchanger. The heat exchanger and the oxygenator are disposed within a housing. The housing is configured to be selectively coupleable with two or more other types of components that become disposed within the internal space when coupled with the housing.

Such a blood oxygenator apparatus may optionally include one or more of the following features. The two or more other types of components may include a pump assembly and an inner wall module. The pump assembly may include a rotary vane member and a stationary member that is coupleable to the housing. The rotary vane member may define a maximum diameter, and may extend from the stationary member by an axial length. In some embodiments, the axial length of the rotary vane member is greater than the maximum diameter of the rotary vane member. The blood oxygenator apparatus may also include a flow distribution element disposed within the internal space or another location within the apparatus. In some embodiments, the flow distribution element is configured to facilitate a substantially uniform radial flow rate of blood entering the heat exchanger.

In another implementation, a method of configuring a blood oxygenator apparatus includes selectively coupling, to a housing of the blood oxygenator apparatus, one component of two or more types of components that are selectively coupleable to the housing of the blood oxygenator apparatus. The blood oxygenator apparatus includes a heat exchanger defining an internal space, and an oxygenator arranged concentrically around the heat exchanger. The one component is disposed within the internal space when the one component is coupled to the housing.

Such a method of configuring a blood oxygenator apparatus may optionally include one or more of the following features. The two or more types of components may include a pump assembly and an inner wall module. The pump assembly may include a rotary vane member and a stationary member that is coupleable to the housing. The rotary vane member may define a maximum diameter. The rotary vane member may extend from the stationary member by an axial length. In some embodiments, the axial length of the rotary vane member is greater than the maximum diameter of the rotary vane member. The pump assembly may be magnetically coupleable with a drive motor. In some embodiments, the blood oxygenator apparatus also includes a flow distribution element disposed within the internal space. In various embodiments, the flow distribution element is configured to facilitate a substantially uniform radial flow rate of blood entering the heat exchanger.

Particular embodiments of the subject matter described in this document can be implemented to realize one or more of the following advantages. In some embodiments, using the devices and methods provided herein, patients can undergo open-heart surgery with less potential for adverse effects. For example, using some embodiments provided herein less dilution of the patient's blood is needed in comparison to conventional extracorporeal circuits. Because of less hemodilution, the potential for the patient's hematocrit to drop below a critical value is lessened. The patient is therefore less likely to need a blood transfusion. In addition, the use of some embodiments described herein provides a simplified extracorporeal circuit in comparison to conventional extracorporeal circuits. Fewer connections are needed. Hence, the potential for leaks from the extracorporeal circuit is reduced. Clean up and decontamination efforts can be thereby mitigated. Additionally, the time required to prepare the extracorporeal circuit is reduced in comparison to conventional extracorporeal circuits. Therefore, a less costly surgical procedure is possible. In some embodiments, the blood oxygenators provided herein are configured to facilitate a desired flow distribution within the blood oxygenator apparatus. For example, in some embodiments a substantially uniform radial flow distribution through the heat exchanger of the apparatus can be attained by configuring a rotary vane member, a flow distribution element, and/or an oxygenator fiber bundle winding density in a selected manner. Accordingly, a heat and/or oxygen exchange efficiency of the blood oxygenator can be enhanced in comparison to equivalent oxygenators that have non-uniform radial flow. Further, some embodiments of the oxygenator devices provided herein are selectively coupleable with two or more other modules, such as a pump module. Accordingly, such oxygenator devices can be advantageously configured as desired by a clinician user.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices used during surgical procedures for the treatment of heart conditions. For example, this document provides extracorporeal circuit devices that can be used for on-pump open-heart surgery to support surgical procedures such as coronary artery bypass grafting.

Figure 1:
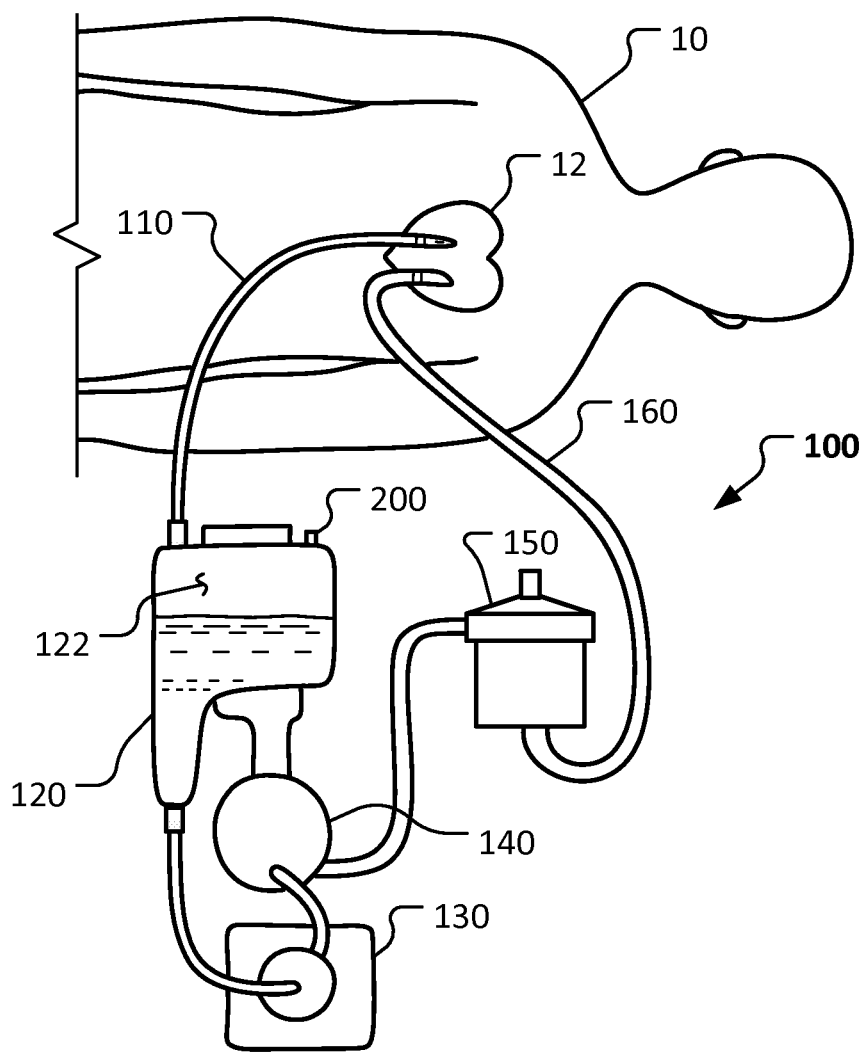
FIG. 1 is a schematic diagram of patient undergoing open-heart surgery while being supported using an extracorporeal circuit in accordance with some embodiments provided herein.

Referring to FIG. 1, a patient 10 can receive medical treatment while using an exemplary conventional extracorporeal blood flow circuit 100. In this illustrative example, the patient 10 is undergoing a heart bypass procedure using the extracorporeal blood flow circuit 100. The circuit 100 is connected to the patient 10 at the patient's heart 12. Blood from the patient 10 is extracted from the patient 10 at the patient's heart 12; the blood is circulated through the circuit 100; and the blood is then returned to the patient's heart 12.

The extracorporeal blood flow circuit 100 includes, at least, a venous tube 110, a blood reservoir 120, a pump 130, an oxygenator 140, an arterial filter 150, and an arterial tube 160. The venous tube 110 is in physical contact with the heart 12 and in fluid communication with the venous side of the circulatory system of the patient 10. The venous tube 110 is also in fluid communication with an inlet to the reservoir 120. An outlet from the reservoir 120 is connected by tubing to an inlet of the pump 130. The outlet of the pump 130 is connected to tubing to an inlet of the oxygenator 140. The outlet of the oxygenator 140 is connected by tubing to an inlet of the arterial filter 150. An outlet of the arterial filter 150 is connected to the arterial tube 160. The arterial tube 160 is in physical contact with the heart 12 and in fluid communication with the arterial side of the circulatory system of the patient 10.

Briefly, the extracorporeal blood flow circuit 100 operates by removing venous blood from the patient 10 via the venous tube 110. Blood from the venous tube 110 is deposited in the reservoir 120. At least some amount of blood is intended to be maintained in the reservoir 120 at all times during the medical procedure. Blood from the reservoir 120 is drawn from the reservoir 120 by the pump 130. The pressure generated by the pump 130 propels the blood through the oxygenator 140. In the oxygenator 140 the venous blood is enriched with oxygen. The oxygen-rich arterial blood exits the oxygenator 140, travels through the arterial filter 150, and is injected into the patient's heart 12 by the arterial tube 160.

One of skill in the art will recognize that the extracorporeal blood flow circuit 100 may contain a significant volume of fluids (e.g., blood from the patient and crystalloid priming solution). A reduction of the fluidic volume within the extracorporeal blood flow circuit 100 is advantageous for the reasons described above. Therefore, combining component of the extracorporeal blood flow circuit 100 is desirable.

Figure 2:
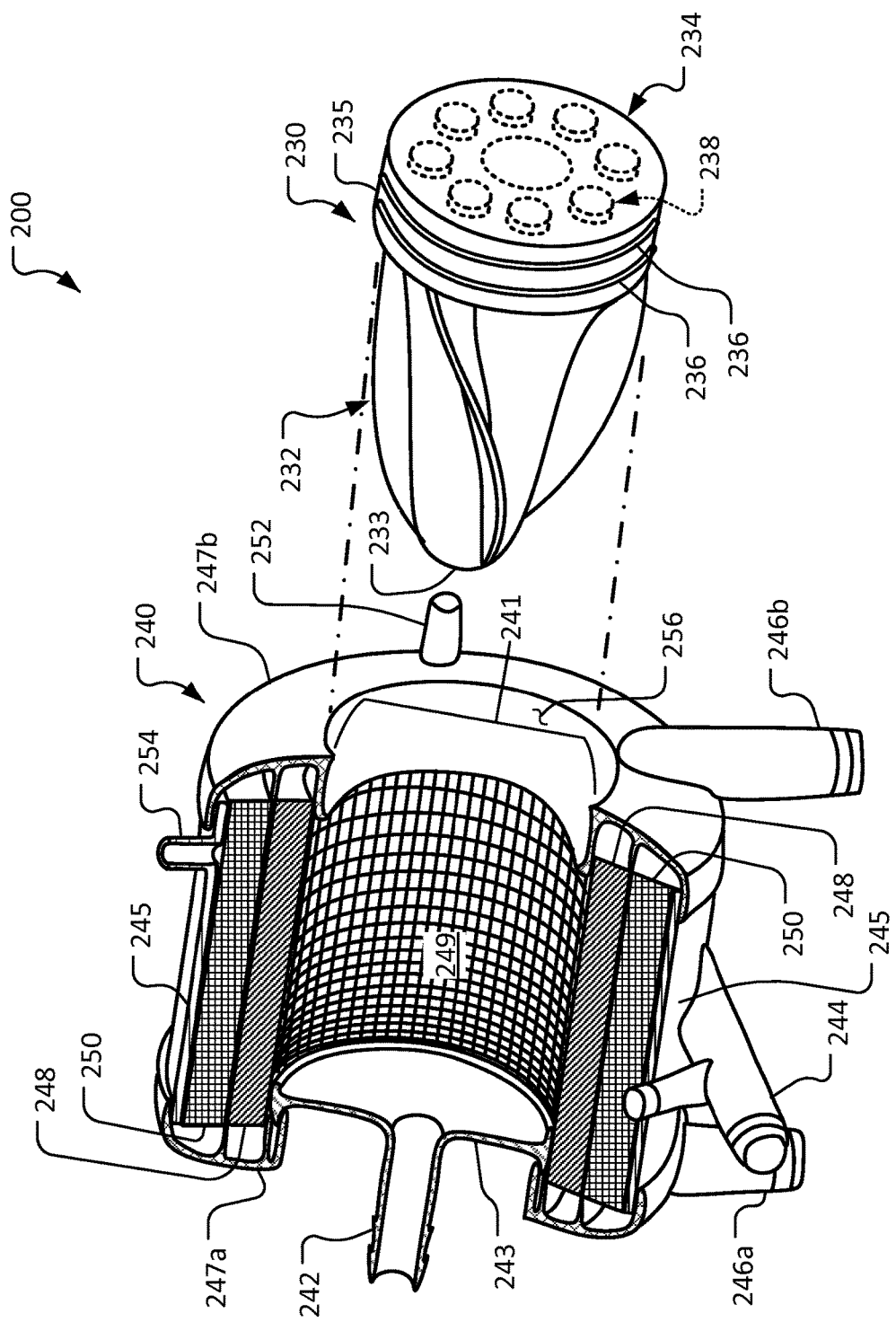
FIG. 2 is an exploded perspective view of an oxygenator that includes an integral pump, in accordance with some embodiments provided herein.

Referring to FIG. 2, an example integrated pump and oxygenator 200 includes a pump module 230 and an oxygenator module 240. In the depicted embodiment, the oxygenator module 240 is designed to receive the pump module 230 within an interior space 241 defined within the oxygenator module 240. As such, an overall more compact extracorporeal circuit can be attained, thereby facilitating a reduction of the hemodilution of a patient being surgically treated using the integrated pump and oxygenator 200. The pump module 230 may also be referred to herein as a pump assembly. The oxygenator module 240 may also be referred to herein as an oxygenator apparatus.

In the depicted embodiment, the pump module 230 is selectively coupleable with the oxygenator module 240. That is, as described further below, the oxygenator module 240 is a universal configuration that can receive various types of other components within the interior space 241. For example, as shown, the oxygenator module 240 can receive the pump module 230 within the interior space 241. In another example, the oxygenator module 240 can receive an inner wall module within the interior space 241 (refer to FIG. 3). In another example, the oxygenator module 240 can receive a heat exchanger (not shown) within the interior space 241. It is envisioned within the scope of this disclosure that still other types of components can be received within the interior space 241 of the oxygenator module 240. In some embodiments, the pump module 230 is reversibly coupleable with the oxygenator module 240. That is, in some embodiments the pump module 230 can be coupled with the oxygenator module 240, and subsequently uncoupled from the oxygenator module 240.

In some embodiments, the end user (e.g., clinician) can determine a desired apparatus configuration and then couple the desired component within the interior space 241 of the oxygenator module 240 in a "plug and play" fashion. For example, on one occasion the end user may determine that it is desirable to couple the pump module 230 within the interior space 241 of the oxygenator module 240 for a particular surgery. On another occasion, the end user may determine that it is desirable to couple an inner wall module within the interior space 241 of the oxygenator module 240 for a particular surgery (and to use a separate pump in the extracorporeal circuit, such as pump 130 of FIG. 1).

In some embodiments, the manufacturing facility may configure the desired component within the interior space 241 of the oxygenator module 240. For example, the manufacturer may configure some oxygenator modules 240 with pump modules 230, and other oxygenator modules 240 with other components such as inner wall modules. In such a scenario, having a universal oxygenator module 240 can be desirable to a manufacturer for a number of reasons, such as inventory reduction, increased production volumes, piece-part cost reductions, reduced changeovers, increased production productivity, and the like.

While the depicted embodiment of the integrated pump and oxygenator 200 is a two-part modular design (i.e., the pump module 230 is selectively coupleable with the oxygenator module 240), in some embodiments the integrated pump and oxygenator 200 is a single-part design (i.e., not modular). That is, in some embodiments a rotary pump member is coupled with the other portions (heat exchanger, oxygenator fiber bundle, housing, etc.) so as to form a generally unitary assembly.

The oxygenator module 240 includes a blood inlet 242 extending from an end wall 243, and a blood outlet 244 extending from a peripheral housing 245. As the blood flows between the blood inlet 242 and the blood outlet 244, the blood passes through a heat exchanger 248 and an oxygenator fiber bundle 250. In some embodiments, one or more filter members may also be included in the blood flow path within the oxygenator module 240. In some embodiments, the heat exchanger 248 defines the interior space 241.

In some embodiments, an optional flow distribution element 249 may be included in the oxygenator module 240. The flow distribution element 249 can facilitate a desired flow distribution (e.g., a substantially uniform radial flow distribution in some embodiments) of blood as the blood passes from the interior space 241 to the heat exchanger 248.

To obtain a desired flow distribution entering the heat exchanger 248, in some embodiments the flow distribution element 249 has multiple openings that are different in relative sizes. For example, to obtain a substantially uniform radial flow distribution (e.g., within about +/−10%) entering all areas of the heat exchanger 248, in some embodiments the flow distribution element 249 has its smallest openings at its end nearest to the blood inlet 242, and other openings that become progressively larger in a direction toward the end opposite of the inlet 242. Hence, in that example, the flow distribution element 249 provides a maximum flow resistance near to the blood inlet 242, and progressively less flow resistance at locations farther away from the blood inlet 242. This progressive distribution of flow resistance can serve to substantially equalize the flow rate of blood entering all areas of the heat exchanger 248. It should be understood that the flow distribution element 249 can be configured with any desired arrangement of different opening sizes, to attain any desired distribution of blood flow entering the heat exchanger 248.

In some embodiments, the flow distribution element 249 is a mesh or a woven material. In some embodiments, the flow distribution element 249 is a molded element. In some embodiments, the flow distribution element 249 is made of other types of constructions.

The flow distribution element 249 can be releasably or permanently affixed to the oxygenator module 240. In some embodiments, the flow distribution element 249 is releasably or permanently affixed to the oxygenator module 240 as part of the manufacturing process of the oxygenator module 240. In some embodiments, the flow distribution element 249 is releasably or permanently affixed to the oxygenator module 240 by an end user.

The flow distribution element 249 can be positioned at various locations on or in the oxygenator module 240. For example, in the depicted embodiment the flow distribution element 249 is disposed on or near to the inner diameter of the heat exchanger 248. Alternatively or additionally, in some embodiments the flow distribution element 249 can be located in one or more positions such as, but not limited to, within the heat exchanger 248, between the heat exchanger 248 and the oxygenator fiber bundle 250, within the oxygenator fiber bundle 250, on the outer diameter of the oxygenator fiber bundle 250, and the like. In some embodiments, two or more flow distribution elements 249 are included in an oxygenator module 240. In some such embodiments, the two or more flow distribution elements 249 are configured differently from each other.

Additionally, or alternatively, in some embodiments the wound-density of the fibers of the oxygenator module 240 may be selectively varied along the axial length of the oxygenator module 240 to facilitate a desired flow distribution (e.g., a substantially uniform radial flow distribution in some embodiments). For example, the fibers of the oxygenator module 240 may be wound such that there is less open space between the fibers within the oxygenator module 240 at the axial end portion where the blood inlet 242 is located in comparison to the opposite axial end portion. Hence, in such an arrangement, blood flowing through the oxygenator module 240 will experience more flow resistance at the axial end portion where the blood inlet 242 is located in comparison to the opposite axial end portion. Such an arrangement may serve to facilitate a substantially uniform radial flow distribution through the entire axial length of the oxygenator 200.

The oxygenator module 240 also includes a first water port 246*a* and a second water port 246*b*. The water ports 246*a* and 246*b* allow the inflow and outflow of water for cooling or heating the blood via the heat exchanger 248. The oxygenator module 240 also includes a gas inlet (not visible) and a gas outlet 252. The gas inlet and outlet 252 allow the inflow and outflow of oxygen-rich gas for oxygenating the blood via the oxygenator fiber bundle 250. The oxygenator module 240 includes two end caps 247*a* and 247*b* that help structurally hold the parts of the oxygenator module 240 together, and that define annular manifolds for the water and oxygen-rich gas. The oxygenator module 240 also includes other parts such as a purge port 254, a component interface feature 256, and other various parts and features known to one of skill in the art.

The pump module 230 includes a rotary vane member 232 and a stationary end cap 234. As described further below, the rotary vane member 232 can spin in relation to the stationary end cap 234. The spinning of the rotary vane member 232 provides the pumping force to pressurize the blood, thereby causing the blood to flow between the blood inlet 242 and the blood outlet 244. In some embodiments, the rotary vane member 232 is configured to facilitate a desired flow distribution (e.g., a substantially uniform flow distribution in some embodiments) of blood as the blood passes from the interior space 241 to the heat exchanger 248. Hence, in some embodiments the rotary vane member 232 has an outer profile that is generally conical or frustoconical. Alternatively, or additionally, the pitch along the axial length of the rotary vane member 232 of the one or more vanes on the rotary vane member 232 may be selected so that the rotary vane member 232 is designed to facilitate a uniform radial flow distribution. That is, in some embodiments the pitch of one or more of the vanes on the rotary vane member 232 may be greater at some portions of the rotary vane member 232 than at other portions of the rotary vane member 232. Alternatively, or additionally, the shape along the axial length of the rotary vane member 232 of the one or more vanes on the rotary vane member 232 may be selected so that the rotary vane member 232 is designed to facilitate a uniform radial flow distribution. That is, in some embodiments the shape (e.g., radial extension, curvatures, angles, etc.) of the one or more vanes on the rotary vane member 232 may be different at some portions of the rotary vane member 232 than at other portions of the rotary vane member 232.

While in the depicted embodiment of the rotary vane member 232 the vanes extend along the entire axial length of the rotary vane member 232, in some embodiments one or more of the vanes may extend only partially along the length of the rotary vane member 232 (e.g., to facilitate a uniform radial flow distribution). In some embodiments, one or more of the vanes extend along the entire axial length of the rotary vane member 232, while one or more other vanes extend only partially along the axial length of the rotary vane member 232. In some embodiments, other structural features can be included to facilitate a uniform radial flow distribution through the heat exchanger 248.

The stationary end cap 234 includes an oxygenator interface feature 235 that configures the pump module 230 to couple with the component interface feature 256 of the oxygenator module 240. The oxygenator interface feature 235 and the component interface feature 256 are complementary with each other such that the pump module 230 can be coupled with the oxygenator module 240 by engaging the oxygenator interface feature 235 and the component interface feature 256.

In the depicted embodiment, the oxygenator interface feature 235 and the component interface feature 256 are configured to linearly snap together. In addition, in some embodiments one or more seals 236 can be included to prevent leakage from the integrated pump and oxygenator 200 in the area of the interface features 235 and 256. In some embodiments, other types of complementary interface features 235 and 256 can be incorporated in design of the integrated pump and oxygenator 200. For example, complementary interface features 235 and 256 can comprise a threaded coupling, a clamp coupling, a tapered coupling, a quarter-turn locking coupling, and the like, and combinations thereof.

In the depicted embodiment, when the pump module 230 is coupled with the oxygenator module 240, the free end 233 of the rotary vane member 232 is separated from (spaced apart from) the end wall 243 of the oxygenator module 240. In some embodiments, when the pump module 230 is coupled with the oxygenator module 240, the free end 233 of the rotary vane member 232 contacts the end wall 243. For example, in some embodiments the free end 233 of the rotary vane member 232 is partially or fully supported by the end wall 243. In some such embodiments, a bearing or other type of sliding rotary interface may be included between the free end 233 of the rotary vane member 232 and the end wall 243.

As described further below, in some embodiments the pump module 230 includes one or more magnets 238. The one or more magnets 238 can be magnetically coupled with a separate drive motor (not shown) that drives the rotary vane member 232 using the magnetic coupling between the drive motor and the one or more magnets 238. As such, the drive motor advantageously does not contact the blood. In some embodiments, other types of couplings between the drive motor and the rotary vane member 232 are included. For example, a geared coupling, friction coupling, and the like can be used in some embodiments as the coupling between the drive motor and the rotary vane member 232.

Figure 3:
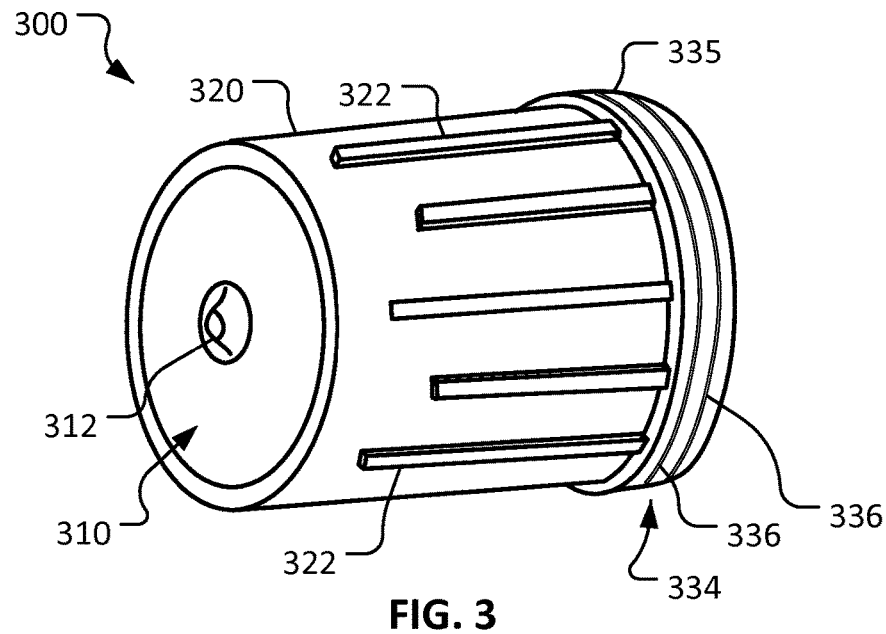
FIG. 3 is a perspective view of an inner wall module that is coupleable with the oxygenator depicted in FIG. 2, in accordance with some embodiments provided herein.

Referring also to FIG. 3, an example inner wall module 300 is configured for selective coupling with the oxygenator module 240. The inner wall module 300 includes an end cap 334, an inlet face 310, and an inner wall 320.

The end cap 334 includes an oxygenator interface feature 335 that is analogous to the oxygenator interface feature 235 described above. The end cap 334 can be selectively coupled with the component interface feature 256 of the oxygenator module 240 by engaging the oxygenator interface feature 335 and the component interface feature 256 using any of the manners described above in reference to oxygenator interface feature 235 and component interface feature 256. In some embodiments, the inner wall module 300 is reversibly coupleable with the oxygenator module 240. That is, in some embodiments the inner wall module 300 can be coupled with the oxygenator module 240 and subsequently uncoupled from the oxygenator module 240.

When the inner wall module 300 is coupled with the oxygenator module 240, a space exists between the inlet face 310 and the end wall 243. In addition, a space exists between the inner wall 320 and the inner diameter of the heat exchanger 248. Those spaces can be used to channel blood flow through the oxygenator module 240 in a desired flow path.

When the inner wall module 300 is coupled with the oxygenator module 240, the blood entering through the blood inlet 242 flows toward the inlet face 310. An optional conical flow diverter 312 extending from the inlet face 310 helps to direct the inflowing blood radially outward. The blood then enters the space between the inner wall 320 and the inner diameter of the heat exchanger 248. In some embodiments, one or more surface features 322 on the inner wall 320 direct and or manage the blood flow in a desired fashion. From the space between the inner wall 320 and the inner diameter of the heat exchanger 248, the blood can flow into the heat exchanger 248. From the heat exchanger 248, the blood can then flow to the oxygenator fiber bundle 250 before exiting from the blood outlet 244. In some embodiments, one or more filter members may also be included in the blood flow path within the oxygenator module 240.

In some embodiments, the profile of the inner wall 320 is tapered such that the space between the inner wall 320 and the inner diameter of the heat exchanger 248 is largest near the end wall 243 and gradually becomes smaller along the direction towards the other end of the oxygenator module 240 (towards component interface feature). Such tapering of the space between the inner wall 320 and the inner diameter of the heat exchanger 248 can help facilitate uniformity of blood flow through the heat exchanger 248 and the oxygenator fiber bundle 250.

One of skill in the art will recognize that when the inner wall module 300 is coupled with the oxygenator module 240, the inner wall module 300 generally completes an outer housing assembly for the oxygenator module 240, along with the end wall 243, the peripheral housing 245, and the end caps 247a and 247b. As such, blood can then flow along a contained pathway between the blood inlet 242 and the blood outlet 244 (and through the heat exchanger 248 and the oxygenator fiber bundle 250).

Figure 4:
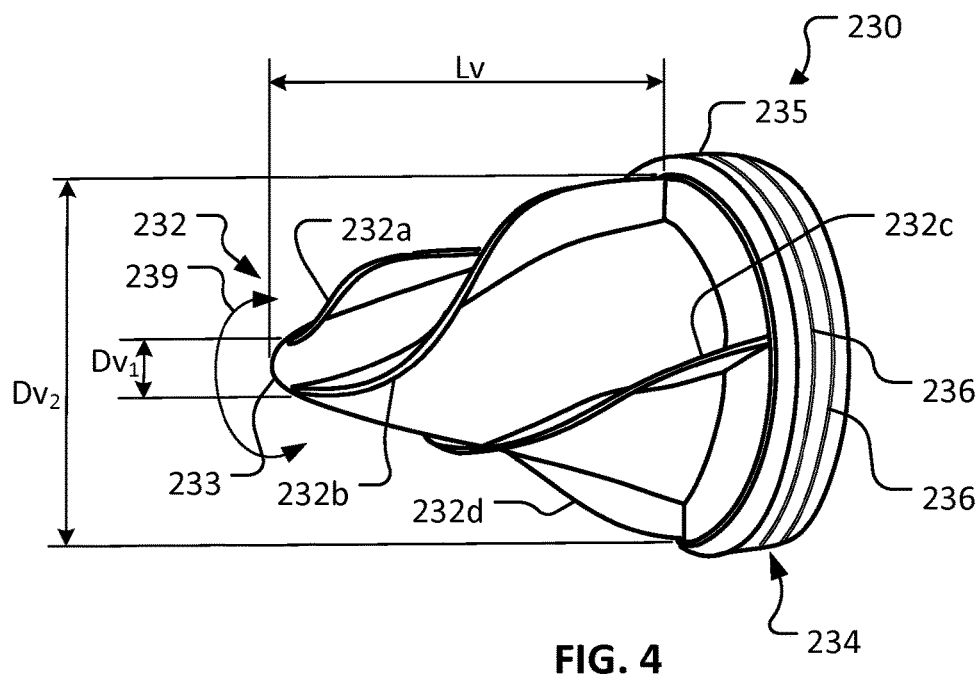
FIG. 4 is a perspective view of an inner pump module that is coupleable with the oxygenator depicted in FIG. 2, in accordance with some embodiments provided herein.

Referring to FIG. 4, in the depicted embodiment, the pump module 230 defines an outer profile that becomes progressively larger along the axial direction from the free end 233 towards the stationary end cap 234. In some embodiments, the outer profile of the pump module 230 is generally conical, frustoconical, pyramidal, and the like. In some embodiments, the rotary vane member 232 may comprise stepped segments or portions of differing outer diameters. When the rotary vane member 232 has an expanding outer profile, it can help to facilitate uniformity of blood flow through the heat exchanger 248 and the oxygenator fiber bundle 250. In some embodiments, the outer profile of the pump module 230 is generally cylindrical.

The rotation of the rotary vane member 232 as depicted by arrow 239. The rotary vane member 232 rotates in relation to the stationary end cap 234.

In the depicted embodiment, the rotary vane member 232 includes four vanes 232a, 232b, 232c, and 232d. In some embodiments, other numbers of vanes are included. For example, in some embodiments one, two, three, five, six, seven, or more than seven vanes are included.

In the depicted embodiment, the outer diameter defined by the rotary vane member 232 (including the four vanes 232a, 232b, 232c, and 232d) is smaller at the free end 233 than at the stationary end cap 234. That is, the free end diameter $Dv_1$ is smaller than the supported end diameter $Dv_2$. In some embodiments, the ratio of the free end diameter $Dv_1$ to the supported end diameter $Dv_2$ is about 1:2 (i.e., the diameter of the rotary vane member 232 at the free end 233 is about one half of the diameter of the rotary vane member 232 at the stationary end cap 234). In some embodiments, that diametric ratio of $Dv_1:Dv_2$ is in a range of about 1:1 to about 1:2, or about 1:2 to about 1:3, or about 1:3 to about 1:4, or about 1:4 to about 1:5, or about 1:5 to about 1:6, or about 1:6 to about 1:7, or about 1:7 to about 1:10, or greater than 1:10. In the depicted embodiment, the supported end diameter $Dv_2$ is the maximum diameter of the rotary vane member 232.

In some embodiments, the rotary vane axial length Lv is a longer distance than the supported end diameter $Dv_2$ (and/or the maximum diameter of the rotary vane member 232). For example, in some embodiments the ratio of the rotary vane axial length Lv to the supported end diameter $Dv_2$ is in a range of about 8:1 to about 10:1, or about 7:1 to about 9:1, or about 6:1 to about 8:1, or about 5:1 to about 7:1, or about 4:1 to about 6:1, or about 3:1 to about 5:1, or about 2:1 to about 4:1, or about 1:1 to about 3:1, or about 1:1 to about 2:1, or about 1:1 to about 1.5:1, or about 2:1.5 to about 1.5:1. In some embodiments, the ratio of the rotary vane axial length Lv to the supported end diameter $Dv_2$ is greater than about 2:1.5, or greater than about 1.5:1, or greater than about 2:1, or greater than about 2.5:1, or greater than about 3:1. In some embodiments, the rotary vane axial length Lv is generally equal to the axial length of the heat exchanger 248.

In the depicted embodiment, the vanes 232a, 232b, 232c, and 232d are attached to the underlying cone along curved paths. In some embodiments, the vanes 232a, 232b, 232c, and 232d are attached to the underlying cone along straight paths. In some such embodiments, the vanes 232a, 232b, 232c, and 232d are attached to the underlying cone along straight paths that, if extended beyond the free end 233, would intersect with the longitudinal axis of the rotary vane 232. In some such embodiments, the vanes 232a, 232b, 232c, and 232d are attached to the underlying cone along straight paths that, if extended beyond the free end 233, would not intersect with the longitudinal axis of the rotary vane 232.

In some embodiments, the vanes 232a, 232b, 232c, and 232d extend from the underlying cone generally radially in relation to the longitudinal axis of the rotary vane 232 (e.g., at 90°). In some embodiments, some or all portions of the vanes 232a, 232b, 232c, and 232d extend from the underlying cone at angles other than 90°, such as in a range from about 30° to about 50°, or from about 40° to about 60°, or from about 50° to about 70°, or from about 60° to about 80°, or from about 70° to about 90°.

In some embodiments, the vanes 232a, 232b, 232c, and 232d extend from the underlying cone by a uniform distance at along the entire length of the vanes 232a, 232b, 232c, and 232d. In some embodiments, the vanes 232a, 232b, 232c, and 232d extend from the underlying cone by non-uniform distances at varying locations along the length of the vanes 232a, 232b, 232c, and 232d. For example, at the free end 233 the vanes 232a, 232b, 232c, and 232d may extend from the underlying cone by distances that are less than the distances that the vanes 232a, 232b, 232c, and 232d extend from the underlying cone at the supported end near the stationary end cap 234. In some embodiments, at a particular axial location along the rotary vane axial length Lv, one or more of the vanes 232a, 232b, 232c, and 232d may extend from the underlying cone by a distance that is unequal to the distance that one or more of the other vanes 232a, 232b, 232c, and 232d extend from the underlying cone. Said more simply, some vanes (or portions thereof) may be longer than other vanes (or portions thereof).

Figure 5:
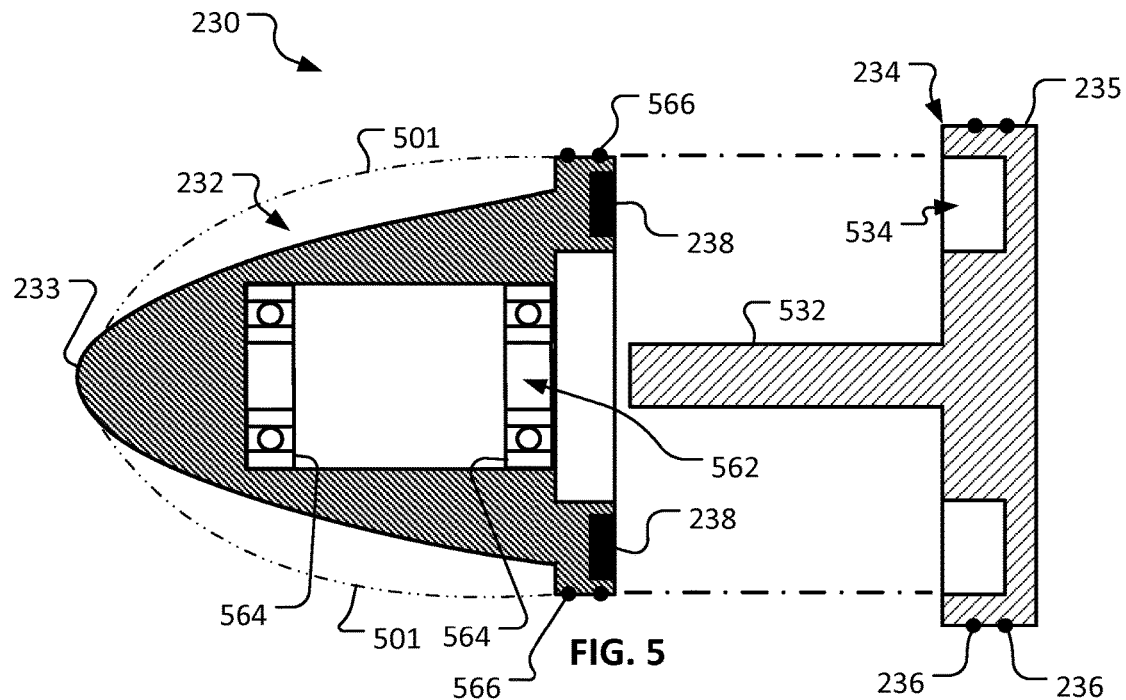
FIG. 5 is an exploded cross-sectional view of an inner pump module that can be integrated with an oxygenator, in accordance with some embodiments provided herein.
Figure 6:
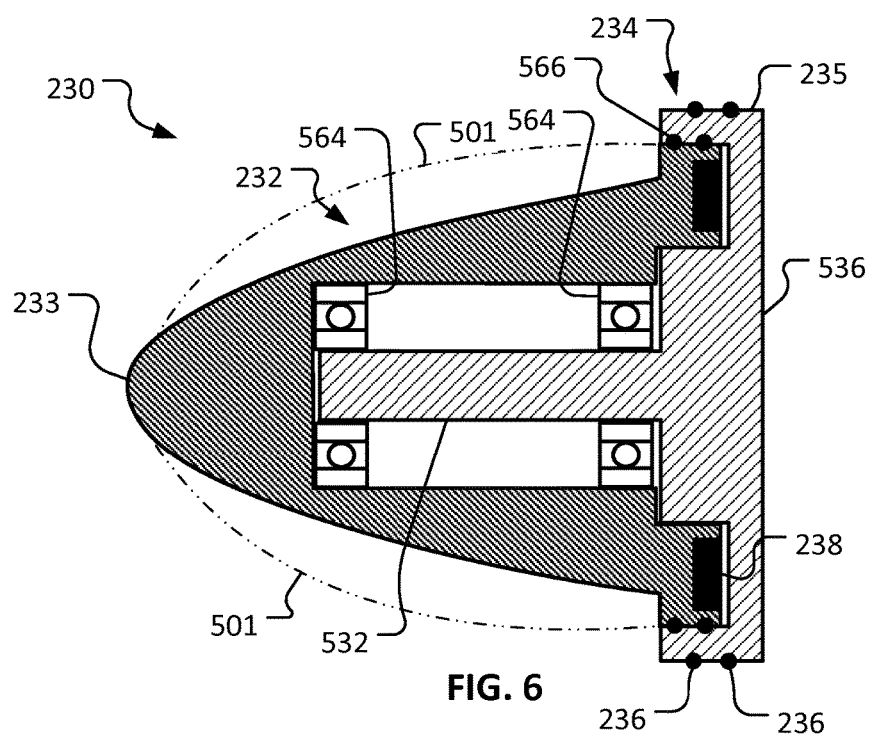
FIG. 6 is a cross-sectional view of the inner pump module of FIG. 5, shown in an assembled configuration.

Referring to FIGS. 5 and 6, the pump module 230 is shown in longitudinal cross-sectional views to illustrate how, in some embodiments, the pump module 230 can be constructed. It should be understood that the depicted design of the pump module 230 is merely exemplary and is non-limiting. That is, other designs of the pump module 230 are also envisioned and within the scope of this disclosure.

In the depicted embodiment, the pump module 230 includes the rotary vane member 232 and the stationary end cap 234. As described above, the rotary vane member 232 can spin in relation to the stationary end cap 234. A cross-section of the envelop defined by the spinning of the rotary vane member 232 of this example embodiment is illustrated by the phantom lines 501.

As described above, in the depicted embodiment the stationary end cap 234 includes the oxygenator interface feature 235 and the one or more seals 236. Additionally, in the depicted embodiment the stationary end cap 234 includes a shaft 532, and an annular recess 534.

As described above, in the depicted embodiment the rotary vane member 232 includes the free end 233 and the one or more magnets 238. The one or more magnets 238 are fixedly attached to the rotary vane member 232. Additionally, in the depicted embodiment the rotary vane member 232 includes a bore 562, one or more bearings 564, and one or more seals 566. The one or more bearings 564 are coupled within the bore 562. The one or more seals 566 are positioned to interface with the stationary end cap 234 to substantially prevent blood ingress into the spaces between the rotary vane member 232 and the stationary end cap 234.

The inner diameters of the one or more bearings 564 receive the shaft 532 of the stationary end cap 234. Accordingly, the inner race of the one or more bearings 564 is coupled with the stationary end cap 234 and the outer race of the one or more bearings 564 is coupled with the rotary vane member 232. The rotary vane member 232 can thereby spin in relation to the stationary end cap 234.

The stationary end cap 234 has a face 536. A drive motor (not shown) can interface with the pump module 230 via the face 536 of the stationary end cap 234. Such a drive motor can magnetically couple with the one or more magnets 238 of the rotary vane member 232. As the drive motor is rotated, the magnetic coupling between the drive motor and the one or more magnets 238 of the rotary vane member 232 will cause the rotary vane member 232 to rotate in a corresponding speed and direction. Therefore, when the pump module 230 is coupled within the oxygenator module 240 (refer to FIG. 2), and the drive motor is rotating the rotary vane member 232, the rotating rotary vane member 232 can pump blood along the pathway between the blood inlet 242 and the blood outlet 244 (and through the heat exchanger 248 and the oxygenator fiber bundle 250).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A blood oxygenator apparatus, comprising:
   a heat exchanger defining an internal space; and
   an oxygenator arranged concentrically around the heat exchanger,
   wherein the heat exchanger and the oxygenator are disposed within a housing, wherein the housing includes a component interface such that the housing is configured to be selectively coupleable with two or more other types of components that become disposed within the internal space when coupled with the housing, wherein the two or more other types of components comprise a pump assembly and an inner wall module.

2. The blood oxygenator apparatus of claim 1, wherein the blood oxygenator apparatus further comprises the pump assembly and the inner wall module.

3. The blood oxygenator apparatus of claim 2, wherein the pump assembly comprises a rotary vane member and a stationary member that is coupleable to the housing, the rotary vane member defining a maximum diameter, the rotary vane member extending from the stationary member by an axial length,
   and wherein the axial length of the rotary vane member is greater than the maximum diameter of the rotary vane member.

4. The blood oxygenator apparatus of claim 1, further comprising a flow distribution element disposed within the internal space.

5. The blood oxygenator apparatus of claim 4, wherein the flow distribution element is configured to facilitate a substantially uniform radial flow rate of blood entering the heat exchanger.

6. A method of configuring a blood oxygenator apparatus, the method comprising:
   selectively coupling to a component interface of a housing of the blood oxygenator apparatus one component of two or more types of components that are selectively coupleable to the component interface of the housing of the blood oxygenator apparatus, wherein the blood oxygenator apparatus comprises:
   a heat exchanger defining an internal space; and
   an oxygenator arranged concentrically around the heat exchanger, wherein the one component is disposed within the internal space when the one component is coupled to the housing, and wherein the two or more types of components that are selectively coupleable to the component interface of the housing comprise a pump assembly and an inner wall module.

7. The method of claim 6, wherein the pump assembly comprises a rotary vane member and a stationary member that is coupleable to the housing, the rotary vane member defining a maximum diameter, the rotary vane member extending from the stationary member by an axial length, and wherein the axial length of the rotary vane member is greater than the maximum diameter of the rotary vane member.

8. The method of claim 6, wherein the pump assembly is magnetically coupleable with a drive motor.

9. The method of claim 6, wherein the blood oxygenator apparatus further comprises a flow distribution element disposed within the internal space.

10. The method of claim 9, wherein the flow distribution element is configured to facilitate a substantially uniform radial flow rate of blood entering the heat exchanger.

* * * * *